United States Patent [19]

Shoher et al.

[11] 4,231,740
[45] Nov. 4, 1980

[54] DENTAL RESTORATIVE STRUCTURES

[76] Inventors: Itzhak Shoher, 50 Shlomo Hamelech St., Tel Aviv; Aharon E. Whiteman, 13 J1 Perez St., Petach Tikvah, both of Israel

[21] Appl. No.: 8,944

[22] Filed: Feb. 2, 1979

[51] Int. Cl.³ .............................................. A61C 13/08
[52] U.S. Cl. ..................................... 433/208; 433/219
[58] Field of Search ............................... 32/2, 8, 9, 10; 433/208, 218

[56] References Cited

U.S. PATENT DOCUMENTS

| 3,052,983 | 9/1962 | Weinstein et al. | 32/12 |
| 3,561,119 | 2/1971 | Susman et al. | 32/12 |

Primary Examiner—Robert Peshock

[57] ABSTRACT

The dental restorative structures of the present invention comprise a porcelain superstructure surrounding a metal substructure composed of a framework of relatively thin metal members interconnected to form concavities within the porcelain superstructure.

13 Claims, 19 Drawing Figures

DENTAL RESTORATIVE STRUCTURES

This invention relates to dental restorative structures having a ceramic porcelain superstructure and a metal substructure and to preformed copings for forming dental restorative structures.

The porcelain to metal dental restoration has become a widely used restoration in fixed prosthodontics. Dental porcelain has excellent optical properties closely simulating the enamel of natural teeth and is readily shaped and arranged to obtain an esthetic quality conforming the restoration to the original tooth. However, porcelain to metal restorations are presently known to experience fracture despite the attention given to their construction. The failure of the porcelain to metal restoration through fracture cannot be explained away by simply attributing it to excessive masticating forces or to unwarranted esthetic concessions during construction.

The construction of a restoration is based upon principals and techniques developed over a great many years. Extensive investigation of construction variables have, in general, been limited to the selection of materials, material composition and characteristics, preparation of the metal surface to assure a satisfactory bond between the metal and porcelain interface and the design and construction of the metal substructure. The metal substructure, which is alternatively referred to in the dental arts as the metal framework or base support, must be sufficiently rigid so as not to deform under the application of force and must be fabricated following proper procedures in order to provide an effective seal between the metal substructure and the prepared tooth form. To satisfy the latter requirement meticulous attention is given to the preparation of the impression, fabrication of the die, formation of the wax pattern, investing procedure and casting method.

Little attention has heretofore been given to the exterior geometry of the metal substructure i.e., the substructure surface geometry which interfaces with the fused porcelain superstructure. In accordance with current practice the wax or plastic pattern, commonly referred to as the coping, is formed with an exterior "thimble" or "cusped thimble" shape geometry. A "thimble shape" coping has a frustoconical curvature whereas the "cusped thimble shape" coping is similar to the thimble shape with raised regions corresponding to the cusps in the crown.

The principal determination in the selection of the coping for a crown or pontic is currently based upon providing as much metal bulk as possible particularly for the pontic. Present practice also dictates forming rounded convex edges whenever possible. The use of a reinforcing collar about the gingival margin is further recommended for added strength.

In accordance with the present invention it has been discovered that the exterior geometry of the metal substructure contiguous to the fused porcelain surface is of paramount importance in avoiding fracture. In fact, porcelain fracture can be substantially reduced by using a metal substructure construction when forming a restored crown having a depending portion forming a partial enclosure with an interior geometry conforming in shape to the prepared tooth and an ascending portion extending from such depending portion toward the occlusal surface of the restoration comprising a plurality of shelf-like members which are preferably interconnected to form a continuum around the restoration. In accordance with the preferred construction the plurality of shelf-like members form a plurality of concavities relative to the exterior surfaces of the restoration, i.e., occlusal, facial, lingual, mesial and distal surfaces respectively. The surfaces of the tooth are identified in this application with conventional dental nomenclature.

The present invention is also applicable to the design of a restorative pontic and bridgework both for anterior and posterior teeth as well as for denture teeth. The distinct advantage in the design of the pontic or bridgework is the ability to use a very limited amount of metal in forming the substructure as will be discussed in more detail hereafter. The preferred design for the restorative pontic is a porcelain superstructure substantially surrounding a metal substruction composed of a framework having a plurality of relatively thin metal braces which are preferably interconnected to form within said porcelain superstructure a plurality of concavities. It is also postulated that by using the substructure designs of the present invention conventional reinforcing collars and shoulders may be eliminated.

The substructure design of the present invention is also directly applicable to the construction of preformed copings for forming the metal substructure of a dental restoration comprising a framework of interconnected members each composed of dental wax or plastic in a predetermined geometry having a plurality of concave surfaces.

Accordingly, it is the principal object of the present invention to provide a ceramo-metal dental restoration which is resistant to fracture.

A further object of the present invention is to provide a ceramo-metal dental restoration which requires less metal in its formation.

A still further object of the present invention is to provide a preformed coping for forming a dental restoration which will automatically provide the predetermined metal substructure design of the present invention.

Other objects and advantages of the present invention will become apparent from the following detailed description of the invention when read in conjunction with the accompanying drawings of which:

Referring now in particular to FIGS. 1A through 1D illustrating a number of molar crown restorations 10, 11, 12 and 13 which were subjected to impact and pressure resistant tests until fracture was experienced. Each of the molar crown restorations include a porcelain superstructure 14, 15, 16 and 17 of equivalent composition and construction covering a metal substruction 18, 19, 20 and 21 respectively. The shape of each substruction 18, 19, 20 and 21, at the interface with the porcelain material, is of a different and predetermined design. Although a great many tests were conducted to determine the influence of the exterior substructure shape on porcelain fracture the present disclosure will refer to only a limited number of such tests to the extent necessary to explain the principals of construction underlying the structural designs for the restorations of the present invention. It is to be understood that the present invention is intended to apply to any dental restoration having a porcelain superstructure and a metal substructure such as, for example, a crown, a pontic, a bridge and a denture tooth.

The composition of the superstructure may be of any conventional porcelain composition preferably a dental porcelain containing a mixture of feldspar, kaolin and quartz. The porcelain may be fired onto the metal substructure following any conventional procedure. The substructure should be of a composition having the proper physical characteristics to resist failure of the restoration through deformation, interfere as little as possible with the esthetics of the restoration and be compatible with the environment of the restoration in the mouth. Accordingly, a semiprecious or precious metal alloy is preferable although non-precious metals and alloys may be used.

Figure 1A:
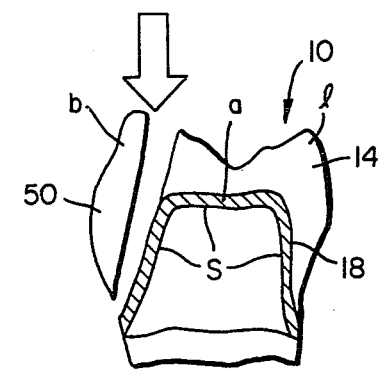
FIG. 1A is a cross-section of a first lower molar crown having a thimble shaped metal substructure which has been fractured by the application of an impact force directed as shown.
Figure 1B:
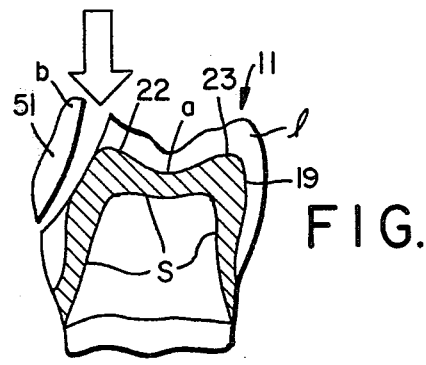
FIG. 1B is a cross-sectional illustration similar to FIG. 1A in which the fractured crown has a cusped thimble shaped metal substructure geometry.
Figure 1C:
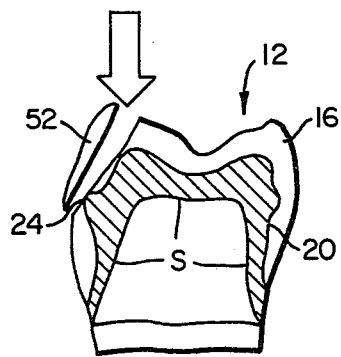
FIG. 1C is a cross-sectional illustration similar to FIG. 1A in which the substructure has a cusped thimble shaped geometry with a circumferential metal belt lying occluso-cervically about the fractured crown.
Figure 1D:
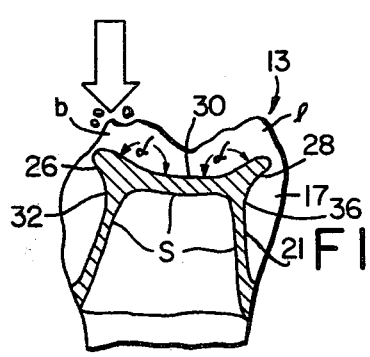
FIG. 1D is a cross-sectional illustration similar to FIG. 1A of a preferred substructure geometry for a restorative molar crown in accordance with the present invention.

The metal substructures 18, 19, 20 and 21 in FIGS. 1A–1D respectively include the conventional thimble shape shown in FIG. 1A, the conventional cusped thimble shape shown in FIG. 1B, and several modified cusped thimble shapes shown in FIGS. 1C and 1D employing the structural design principles of the present invention. The thimble shaped construction can be visualized as a quadrilateral pyramid with a substantially frustoconical geometry. The base surface "a" of the metal thimble shaped superstructure is substantially flat. In the cusped thimble shape as shown in FIG. 1B the base surface "a" is rounded to form two ridges 22 and 23 conforming to the shape of the cusps "b" and "1" on the buccal and lingual surfaces of the restoration. The modified cusped thimble shape shown in FIG. 1C is provided with a circumferential metal protuberance or belt 24 located occlusocervically about the substructure 20. The substructure 21 shown in FIG. 1D is the preferred construction of the present invention and is substantially thimble shaped with the addition of thin metal shelf-like members 26 and 28 extending mesial-distally on the buccal and lingual surfaces of the restoration. The shelves 26 and 28 should lie in a preferably slanted position directed toward the buccal and lingual cusps "b" and "1" of the crown 13 to form a wide occlusal surface with an included angle "α" between each shelf and the base of the substructure in a range between 90 and 180 degrees. With the shelves 26 and 28 properly slanted a plurality of concave surfaces 30, 32 and 36 are formed in the occlusal, buccal and lingual sides of the restoration. With the shelves 26 and 28 interconnected as will be explained hereafter concavities are also formed in the mesial and distal sides of the restoration. The importance of forming concavities will be discussed hereinafter.

Figure 2:
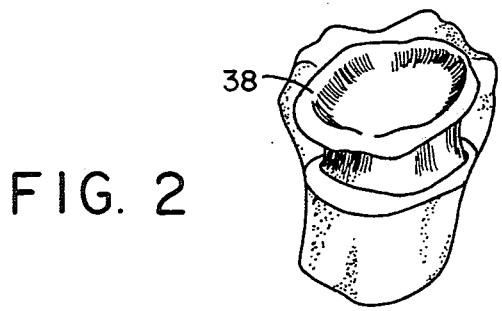
FIG. 2 is a perspective view of a molar crown having the preferred substructure geometry of the present invention with the porcelain superstructure shown in transparent form.

Although the use of at least two shelves 26 and 28 will, by themselves, substantially improve the fracture resistance of the porcelain superstructure 17, particularly to incisal forces, it is preferable to join the shelves interproximally on the mesial and distal sides so as to form a single continuum 38 as is clearly shown in FIG. 2 around the periphery of the substructure. The continuum 38 extends like the brim of a hat with a preferably contour slanted upwardly so as to form a cross-section as shown in FIG. 1D. The resultant molar crown substructure shape forms a depending portion adapted to be secured to the prepared tooth and an ascending portion as hereinabove explained representing a plurality of individual shelves extending from the depending portion or a continuum of shelves surrounding the base of the substructure. The shelves 26 and 28 or the continuum of shelves 38, should be properly oriented to form concavities relative to the exterior surfaces of the restoration. It should be noted in this regard that the metal substructure is to be constructed in a conventional manner starting from a wax or plastic coping having an exterior shape conforming to the teachings of the present invention and an interior shaped contour "s" conforming to the prepared tooth form.

The wax or plastic coping for the substructure may be prefabricated in a conventional fashion into one of the configurations of the present invention for immediate use by a dental laboratory. In forming the metal substructure for a pontic or denture the wax or plastic coping will be constructed in a shape as will be elaborated upon hereafter with reference to FIGS. 6–10. The preformed coping is then invested in a conventional manner to form a duplicate metal substructure geometry in conformity with the conventional "lost wax" technique. On the other hand, for a restorative crown additional wax will have to be added to the interior of the preformed plastic or wax coping which may then be pressed over a die to establish a conforming impression of the prepared tooth. Thereafter the wax or plastic coping may then be invested in a conventional manner for forming the metal substructure. Any conventional wax or plastic composition commercially available to dentists may be used in making the copings.

Figure 3:
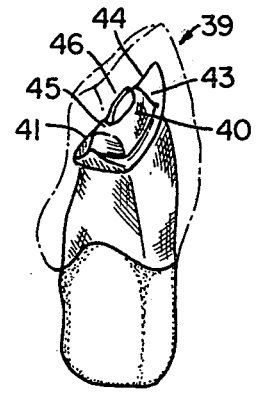
FIG. 3 is a perspective view of an incisor crown having the preferred substructure geometry of the present invention with the porcelain superstructure shown in transparent form.

An upper central incisor crown 38 is shown in FIG. 3 having a metal substructure 40 with shelves 41 and 43 interconnected at the interproximal surfaces to form a single continuum 44 surrounding the periphery of the substructure. The continuum 44 is preferably formed gingival to the base 45 of the substructure and slanted upwardly in a direction toward the buccal and lingual surfaces to form concave areas relative to the incisal, buccal and lingual surfaces of the restoration. An additional plate-like member 46 extends from the base 45 of the substructure 40 toward the incisal edge of the restoration for increasing resistance to fracture from palatal forces. The use of a thin plate-like member 46 may be used with posterior teeth but is particularly advantageous for restoring anterior teeth.

The impact strength of each porcelain restoration shown in FIGS. 1A through 1D was tested using a 100 gram iron cylinder (not shown). The iron cylinder was permitted to fall freely from a predetermined height above the restoration which was controllably varied from 0.2 to 1.5 meters. The cylinder fell directly on a metal pin (not shown) touching the porcelain superstructure 10 at a location on the occlusal surface over a buccal cusp as indicated by the arrow. The height was increased until observable fracture occurred. The pressure bearing capability of the porcelain superstructure was also tested using a conventional Ingstrum machine.

In FIG. 1A the whole buccal porcelain wall 50 of the first molar crown 10 broke off with an impact force from the 100 gram weight falling from a height of 0.2 meters. To cause a similar fracture in the porcelain wall 51 of the molar crown 11 required the 100 gram weight to be raised to a height of 0.6 meters. The addition of the metal belt 24 in FIG. 1C gingival to the buccal cusp "b" limited the extent of fracture to a much smaller porcelain wall area 52 and required a 100 gram weight to be lifted to the height of 1 meter before fracture occurred. Using the preferred design with the shelves 26 and 28 on the buccal and lingual sides respectively, required a height of 1.5 meters to result in a fracture. Moreover, the extent of the fracture was limited to local porcelain crushing and chipping about the vicinity of the buccal cusp "b".

The pressure bearing tests were conducted using a conventional Ingstrum machine in which pressure was increasing applied to the buccal edge of the superstructure through a hard metal core (not shown) in the same location over the buccal cusp "b", as applied in the impact tests, until porcelain breakage occurred. For the FIG. 1A configuration 140 Kg of pressure was necessary to cause breakage. For the FIG. 1B configuration 210 Kg of applied pressure was required to cause porcelain breakage whereas for the modified cusped thimble shape substructure configuration of FIG. 1D 250 Kg was required. In the crown restoration 13 having the substructure design of the present invention no apparent damage was observed even at a pressure as high as 350 Kg.

Figure 4A:
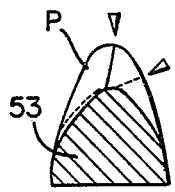
FIGS. 4A–4D are cross-sectional views of metal stud substructures of varying geometry with a fused porcelain superstructure for illustrating the effect of geometry on fracture pattern.
Figure 4B:
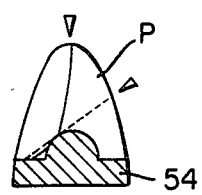
Figure 4C:
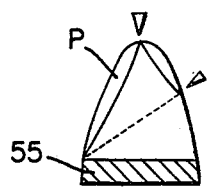
Figure 4D:
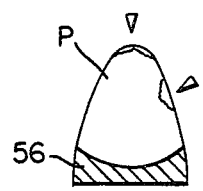

In FIGS. 4A–4D a number of metal studs 53, 54, 55 and 56 were fired over with porcelain in a conventional manner to form a porcelain superstructure p. The porcelain bodies were then subjected to impact forces in the directions indicated until fracture occurred. A substantial resistance to fracture was observed where the metal surface formed a concavity around the porcelain superstructure. A 100 gram weight was used to test for fracture resistance in each configuration with the height of the weight varied until fracture was experienced. The angle at which the impact force was applied was also varied. The weakest configuration was that of FIG. 4A representing the conventional convex shape. The second weakest was that of FIG. 4B followed by that of FIG. 4C simulating the conventional thimble coping design. The strongest design was that of FIG. 4D wherein the porcelain body is fired over a concave metal surface.

It has been demonstrated in accordance with the foregoing tests that when porcelain is fired over a convex metal surface the porcelain becomes weaker as its body depth thickens, and beyond a certain thickness it may fracture spontaneously. Alternatively, porcelain fired over a concave metal surface will not significantly weaken with increases in body thickness, and when fracture does occur it is very localized leaving the main porcelain body unharmed. Moreover, porcelain is more susceptible to fracture when the metal interface plane is parallel to the direction of the impact, and becomes stronger as the plane becomes perpendicular. Metal members or shelves extending from a metal surface increase the porcelain strength, change the direction of the fracture, and will for perpendicular impact forces prevent breakage altogether.

Figure 5A:
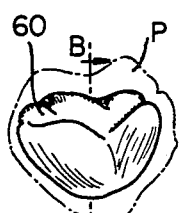
FIG. 5A is a perspective view of a conventional molar pontic restoration with the porcelain superstructure shown as a transparent body.
Figure 5B:
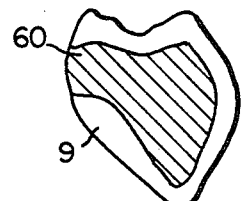
FIG. 5B is a cross-sectional view of the pontic restoration of FIG. 5A taken along the lines 5—5 of FIG. 5A.

A conventional pontic design is shown in FIGS. 5A and 5B. The substructure 60 is a solid mass of metal. In accordance with the design principles underlying the present invention not only is the amount of metal used in fabricating a pontic drastically reduced but the fracture resistance to impact and pressure forces is substantially and simultaneously improved.

Figure 6A:
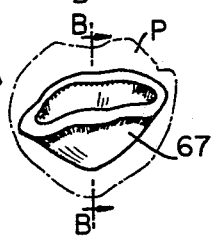
FIG. 6A is a perspective view of a preferred molar pontic restoration design in accordance with the present invention with the porcelain superstructure shown as a transparent body.
Figure 6B:
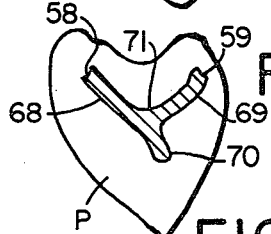
FIG. 6B is a cross-sectional view of the pontic restoration of FIG. 6A taken along the lines 6—6 of FIG. 6A.
Figure 8:
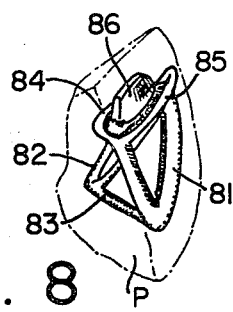
FIG. 8 is a perspective view of the preferred construction for a central incisor pontic in accordance with the present invention with its porcelain superstructure shown in transparent form.
Figure 9:
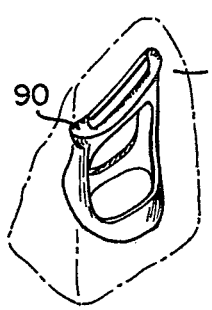
FIG. 9 is a partial perspective view of a denture incisor tooth showing the preferred metal substructure of the present invention with a superstructure in transparent form.
Figure 10:
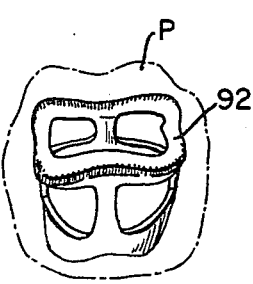
FIG. 10 is another partial perspective view of a molar crown for a denture in accordance with the present invention with a porcelain superstructure.

Two preferred and alternative constructions for the molar pontic of the present invention is shown in FIGS. 6A, 6B and FIGS. 7A and 7B respectively. The preferred design for an anterior pontic in accordance with the present invention is shown in FIG. 8. The preferred designs for the interior framework for a denture tooth is shown in FIGS. 9 and 10 respectively. A dental porcelain material is in each instance fired over the substructure identified by the common reference letter "p" which preferably completely surrounds the substructure particularly for the pontic and denture designs. The substruction 67 in FIG. 6A is a hollow metal cavity having a cross-sectional geometry in the shape of the capital letter "Y" as shown in FIG. 6B with a plurality of extended arms 68, 69 and 70 respectively. The arms 68, 69 and 70 interconnect to form the cavity and are comparable in function to the extended shelves 26 and 28 of the molar crown in that they form concave surfaces relative to the porcelain superstructure "p" in at least the occlusal, facial and lingual surfaces of the restoration. The arms 68 and 69 extend mesio-distally from a common vertex 71 in an inclined position directed toward the buccal and lingual ridges of the restoration. The arms 68 and 69 may be straight or slightly arched and preferably terminate to form concave depressions 58 and 59. The arm 70 joins the arms 68 and 69 at the vertex 71 and lies in a mesio-distal direction substantially intermediate the buccal and lingual surfaces.

Figure 7A:
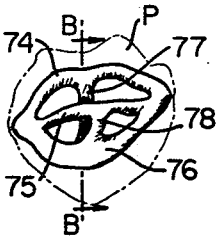
FIG. 7A is a perspective view of another preferred molar pontic restoration design in accordance with the present invention with the porcelain superstructure shown as a transparent body.
Figure 7B:
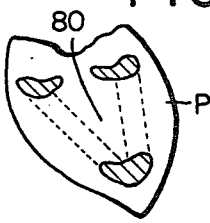
FIG. 7B is a cross-sectional view of the pontic restoration of FIG. 7A taken along the lines 7—7 of FIG. 7A.

The alternative substructure 72, shown in FIG. 7A, employs the least amount of metal of all of the preferred configurations. However, where the metal selected for substructure 72 is not particularly rigid having a modulus of elasticity of below about 16,000 psi the configuration of FIG. 6A is preferable. The metal substructure 72 of FIG. 7A comprises a plurality of flattened relatively thin metal rods or braces 74, 75, 76, 77 and 78 interconnected to one another to form an open framework of interconnected members having a generally "U" shaped cross-section indicated in FIG. 7B forming a large occlusal concavity 80 with a substantial depth of porcelain occluso-cervically. The braces 74 and 75 extend mesio-distally on the buccal and lingual sides of the restoration. The brace 76 also extends mesio-distally from a position intermediate the buccal and lingual surfaces and join the braces 74 and 75 in the interproximal. The braces 77 and 78 extend occluso-cervically on the buccal and lingual sides respectively intermediate the mesial and distal surfaces. The braces 74 and 75 form a closed path of generally elliptical geometry. In this respect the concave depressions 58 and 59 also form a closed path of generally elliptical geometry.

The central pontic construction shown in FIG. 8 has a plurality of flattened metal rods 81, 82 and 83 which extend gingivally from two metal shelves 84 and 85 joined in the interproximal. The metal rods 81 and 82 are looped in the shape of a "U" on the buccal and lingual sides and joined together buccolingually by means of the rod 83. The shelves 84 and 85 form a concavity relative to the incisal edge and may be connected to form a basin for supporting an additional plate 86 extending upright toward the incisal edge of the restoration. The denture teeth shown in FIGS. 9 and 10 have an interior metal framework 90, 92 which is similar in construction to the open pontic framework of FIGS. 8 and 7 respectively. In all cases the framework is composed of a plurality of relatively thin members interconnected in a predetermined geometrical arrangement to form a plurality of concavities within the porcelain superstructure preferably with respect to all exterior surfaces of the restoration.

It should be noted that the metal substructure design of the present invention establishes a state of compression within the dental restoration. It is this state of compression that is primarily responsible for the substantial increase in the resistance to porcelain fracture independent of the porcelain composition. A compressive state is developed even when using only a framework of rods or braces because of the differences in thermal contraction rates between the metal rods or braces and the surrounding porcelain. The surrounding porcelain prevents the metal rods from shrinking which results in compression of the porcelain at the interface. The concave geometries prevents the metal from pulling away at the interface and acts to place the entire porcelain body under compression. This is also true for the metal substructure crown design with shelves arranged to form concavities. With the entire porcelain body under compression there is no area vulnerable to fracture. Moreover, in accordance with the construction of the present invention the shelves and braces extend in directions which lie perpendicular to the direction of external impact. A force directed perpendicular to the interface will have to propagate through compressed porcelain and accordingly enhance porcelain fracture resistance. Metal alloys having a high modulus of elasticity and/or high thermal contraction characteristics are in general preferred for the substructure.

What is claimed is:

1. A dental restoration comprising a molar pontic having a porcelain superstructure surrounding a metal framework composed of an integral assembly of metal members in an open structural arrangement having a basket-like configuration for forming a substantial occlusal concavity with porcelain disposed about, between and below said metal members.

2. A dental restoration as defined in claim 1 wherein said metal framework has a cross-section substantially in the shape of the letter "U".

3. A dental restoration as defined in claim 2 wherein said metal framework has a modulus of elasticity of above about 16,000 psi.

4. A dental restoration comprising an anterior pontic having a porcelain superstructure surrounding a metal framework composed of an integral assembly of metal members in an arrangement including a first section for forming a concave area relative to the incisal edge of said pontic and a second section including a plurality of said metal members interconnected in the form of an open truss extending gingivally from said first section with porcelain disposed about, between and below the members in said second section.

5. A dental restoration as defined in claim 4 further comprising an additional metal member having a substantially flat shelf-like shape extending substantially upright toward the incisal edge of said pontic.

6. A dental restoration as defined in claim 5 wherein said first section includes a curved member forming a depression representing said concave area.

7. A dental coping for forming the metal framework of a pontic in a dental restoration comprising an integral assembly of members interconnected in an open structural arrangement forming a truss with each member composed of a material selected from the class consisting of wax or plastic.

8. A dental coping as defined in claim 7 wherein said truss has a basket-like configuration with a cross-section substantially in the shape of the letter "U".

9. A dental coping as defined in claim 7 wherein said truss has at least one triangular section supporting a base member having a relatively concave surface geometry relative to the incisal edge of the pontic.

10. A dental coping as defined in claim 9 further comprising a substantially flat plate-like member extending upright from said base member.

11. A dental restoration comprising the clinical crown of a tooth having a substructure of metal enclosed within a superstructure of porcelain with said metal substructure having a depending portion forming a partial enclosure with an anterior geometry conforming in shape to the prepared tooth and an ascending portion surrounding said depending portion and extending from said depending portion toward the occlusal surface of the restoration to form a substantially annular concavity relative to such occlusal surface.

12. A dental restoration as defined in claim 11 wherein said ascending portion comprises a continuum of shelf-like members.

13. A dental restoration as defined in claim 11 further comprising a flat metal member extending upright from said depending portion toward the occlusal surface of said restoration.

* * * * *